United States Patent [19]
Copp et al.

[11] Patent Number: 6,005,142
[45] Date of Patent: Dec. 21, 1999

[54] PROCESS FOR PREPARING BENZYL-SUBSTITUTED RHODANINE DERIVATIVES

[75] Inventors: James D Copp, Greenwood; Francis O Ginah; Marvin M. Hansen, both of Indianapolis, all of Ind.

[73] Assignee: Eli Lilly and Company, Indianapolis, Ind.

[21] Appl. No.: 09/029,476

[22] PCT Filed: Sep. 3, 1996

[86] PCT No.: PCT/US96/14101

§ 371 Date: Feb. 25, 1998

§ 102(e) Date: Feb. 25, 1998

[87] PCT Pub. No.: WO97/09305

PCT Pub. Date: Mar. 13, 1997

[51] Int. Cl.⁶ .................................................. C07C 323/29
[52] U.S. Cl. ........................................... 564/162; 548/186
[58] Field of Search ............................................... 564/162

[56] References Cited

U.S. PATENT DOCUMENTS

| | | | |
|---|---|---|---|
| 5,216,002 | 6/1993 | Gidda et al. | 514/369 |
| 5,356,917 | 10/1994 | Panetta | 514/369 |
| 5,387,690 | 2/1995 | Gidda et al. | 548/186 |
| 5,523,314 | 6/1996 | Bue-Valleskey et al. | 514/369 |
| 5,563,277 | 10/1996 | Hansen | 548/182 |

FOREIGN PATENT DOCUMENTS

| | | | |
|---|---|---|---|
| 0 211 670 A2 | 2/1987 | European Pat. Off. | A61K 31/39 |
| 0 391 644 A2 | 10/1990 | European Pat. Off. | C07D 277/14 |
| 0 434 394 A2 | 6/1991 | European Pat. Off. | C07D 277/14 |
| 0 500 337 A1 | 8/1992 | European Pat. Off. | A61K 31/38 |

OTHER PUBLICATIONS

Tetrahedron Letters, 35:38, 6971–6974 (1994).
Tetrahedron: Asymmetry, 7:9, 2515–2518 (1996).
Heterocycles, 48:7, 1307–1312 (1998).

*Primary Examiner*—Robert Gerstl
*Attorney, Agent, or Firm*—Suzanne M. Harvey; Nelson L. Lentz

[57] ABSTRACT

The instant invention provides a novel process for preparing benzyl-substituted rhodanine derivatives. Also provided are novel benzyl-substituted thiolamides and benzyl-substituted hemithioacetals. Such compounds are useful as intermediates in preparing the compounds by the process of the instant invention.

4 Claims, No Drawings

PROCESS FOR PREPARING BENZYL-SUBSTITUTED RHODANINE DERIVATIVES

This application is A 371 of PCT/US96/14101 Sep. 3, 1996.

FIELD OF THE INVENTION

This invention relates to a process for preparing certain benzyl-substituted rhodanine derivatives useful for treating inflammation, inflammatory bowel disease, allergies, arthritis, hypoglycemia and muscular dystrophy and in preventing ischemia induced cell damage.

BACKGROUND OF THE INVENTION

Benzyl-substituted rhodanine derivatives are known to be active in treating inflammation, inflammatory bowel disease (hereinafter IBD), allergies, arthritis, hypoglycemia and muscular dystrophy and in preventing ischemia induced cell damage. For example, U.S. Pat. No. 5,216,002 discloses that certain benzyl-substituted rhodanine derivatives are useful for treating IBD; U.S. Pat. No. 5,158,966 discloses the use of such compounds for treating Type I diabetes; EPO Publication No. 391644 discloses the effectiveness of such compounds for treating inflammation, arthritis and muscular dystrophy, and for preventing ischemia induced cell damage; EPO Publication No. 343643 describes the use of such compounds for treating allergies and inflammation; while EPO Publication No. 587377 discloses these compounds as being effective in treating hypoglycemia.

All of the above patents and publications describe various processes for making the benzyl-substituted rhodanine derivatives disclosed therein. For example, U.S. Pat. No. 5,158,966, herein incorporated by reference, discloses a process for preparing benzyl-substituted rhodanine derivatives comprising reacting 3,5-di-tert-butyl-4-hydroxy benzaldehyde with rhodanine in acetic acid to form 5-{[3,5-bis(1,1-dimethylethyl)-4-hydroxyphenyl]methylene-2-thioxo-4-thiazolidinone, and reducing the resultant 2-thioxo-4-thiazolidinone with hydrogen using palladium on carbon as a catalyst.

Alternately, the alkene of the 2-thioxo-4-thiazolidinone can be reduced by refluxing with diethyl 1,4-dihydro-2,6-dimethyl-3,5-pyridinedicarboxylate, followed by reduction of the thioxo group with hydrogen and palladium on carbon. In another process, reduction of the thioxo group may be accomplished by heating the methyl-2-thioxo-4-thiazolidinone in a mixture of acetic acid in the presence of zinc.

The current processes for preparing benzyl-substituted rhodanine derivatives, as set forth above, have utility. However, these processes require either large amounts of expensive catalyst or generate excessive amounts of environmentally hazardous zinc waste.

The present invention provides an improved process for preparing benzyl-substituted rhodanine derivatives. The process of the present invention can be performed with inexpensive, readily available reagents and eliminates the generation of zinc waste. Other objects, features and advantages of the present invention will become apparent from the subsequent description and the appended claims.

SUMMARY OF THE INVENTION

The present invention provides a process for preparing a compound of the formula

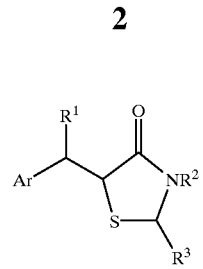

(I)

wherein:

Ar is (i) phenyl, (ii) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, Cl, hydroxy, phenoxy, $C_1$–$C_4$ alkyloxyphenyl, thiophenyl, $C_1$–$C_4$ alkylthiophenyl, $N(R^4)_2$ where each $R^4$ is independently $C_1$–$C_6$ alkyl or (iii) 1- or 2-napthyl;

$R^1$ is H, $C_1$–$C_6$ alkyl, $C_1$–$C_4$ alkyiphenyl, phenyl or phenyl-substituted with one or two substituents independently selected from Cl, F, $C_1$–$C_4$ alkyl, $C_1$–$C_4$ alkoxy, trifluoromethyl, —N($C_1$–$C_4$ alkyl)$_2$ or $C_1$–$C_4$ alkylthio;

$R^2$ is H, $C_1$–$C_6$ alkyl, benzyl or α-methylbenzyl; and $R^3$ is (i) H, (ii) $C_1$–$C_6$ alkyl, (iii) phenyl, (iv) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, Cl, hydroxy, phenoxy, $C_1$–$C_4$ alkyloxyphenyl, thiophenyl, $C_1$–$C_4$ alkylthiophenyl, $N(R^4)_2$ where each $R^4$ is independently $C_1$–$C_6$ alkyl or (v) 1- or 2-napthyl;

which process comprises reacting a compound of the formula III

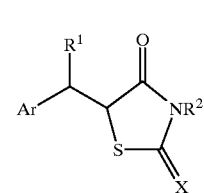

(III)

wherein:

Ar, $R^1$ and $R^2$ are as defined above, and X is S, NH, or O;

with with an aldehyde of the formula

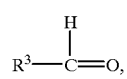

where $R^3$ is as defined above, wherein said reaction is conducted in the presence of an amine of the formula $H_2NR^6$ where $R^6$ is H, $C_1$–$C_6$ alkyl, benzyl or α-methylbenzyl.

The present invention, further, provides new intermediate compounds of the formula II

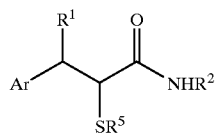

(II)

wherein:
- Ar is (i) phenyl, (ii) phenyl substituted with from one to three substituents independently selected from $C_1-C_8$ alkyl, $C_2-C_6$ alkenyl, $C_2-C_6$ alkynyl, $C_1-C_8$ alkoxy, $C_1-C_8$ alkylthio, trifluoromethyl, $C_1-C_4$ alkylphenyl, phenyl, F, Cl, hydroxy, phenoxy, $C_1-C_4$ alkyloxyphenyl, thiophenyl, $C_1-C_4$ alkylthiophenyl, $N(R^4)_2$ where each $R^4$ is independently $C_1-C_6$ alkyl or (iii) 1- or 2-naphthyl;
- $R^1$ is H, $C_1-C_6$ alkyl, $C_1-C_4$ alkylphenyl, phenyl or phenyl-substituted with one or two substituents independently selected from Cl, F, $C_1-C_4$ alkyl, $C_1-C_4$ alkoxy, trifluoromethyl, —$N(C_1-C_4$ alkyl$)_2$ or $C_1-C_4$ alkylthio;
- $R^2$ is H, $C_1-C_6$ alkyl, benzyl or α-methylbenzyl; and
- $R^5$ is H, —$CHR^3OH$, where $R^3$ is (i) H, (ii) $C_1-C_6$ alkyl, (iii) phenyl, (iv) phenyl substituted with from one to three substituents independently selected from $C_1-C_8$ alkyl, $C_2-C_6$ alkenyl, $C_2-C_6$ alkynyl, $C_1-C_8$ alkoxy, $C_1-C_8$ alkylthio, trifluoromethyl, $C_1-C_4$ alkylphenyl, phenyl, F, Cl, hydroxy, phenoxy, $C_1-C_4$ alkyloxyphenyl, thiophenyl, $C_1-C_4$ alkylthiophenyl, $N(R^4)_2$ where each $R^4$ is independently $C_1-C_6$ alkyl or (v) 1- or 2-napthyl.

The compounds of formula II are useful as intermediates in preparing the compounds of formula I.

DETAILED DESCRIPTION OF THE INVENTION

As used herein, the term "$C_1-C_8$ alkyl" refers to straight and branched chain aliphatic radicals of 1–8 carbon atoms. Typical $C_1-C_8$ alkyl groups include methyl, ethyl, propyl, isopropyl, butyl, isobutyl, sec-butyl, tert-butyl, n-pentane, iso-pentane, n-hexane, iso-hexane and the like. The term "$C_1-C_8$ alkyl" includes within its definition the terms "$C_1-C_4$ alkyl" and "$C_1-C_6$ alkyl".

The term "$C_1-C_8$ alkoxy" represents a straight or branched alkyl chain having 1 to 8 carbon atoms which chain is attached to the remainder of the molecule by an oxygen atom. Typical $C_1-C_8$ alkoxy groups include methoxy, ethoxy, propoxy, isopropoxy, butoxy, isobutoxy, sec-butoxy, tert-butoxy, pentoxy, hexoxy and the like. The term "$C_1-C_8$ alkoxy" includes within its definition "$C_1-C_4$ alkoxy".

The term "$C_2-C_6$ alkenyl" refers to straight and branched chains of 2 to 6 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene and the like.

The term "$C_2-C_6$ alkynyl" refers to straight and branched chains of 2 to 6 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne and the like.

The term "$C_1-C_8$ alkylthio" represents a straight or branched alkyl chain having one to eight carbon atoms, which chain is attached to the remainder of the molecule by a sulfur atom. Typical $C_1-C_8$ alkylthio groups include methylthio, ethylthio, n-propylthio, isopropylthio, n-butylthio, t-butylthio and the like. The term "$C_1-C_8$ alkylthio" includes within its definition "$C_1-C_4$ alkylthio".

"$C_1-C_4$ alkylphenyl" represents a straight or branched chain alkyl group having from one to four carbon atoms attached to a phenyl ring. Typical $C_1-C_4$ alkylphenyl groups include methylphenyl, ethylphenyl, n-propylphenyl, isopropylphenyl, n-butylphenyl, isobutylphenyl, and tert-butylphenyl.

The term "$C_1-C_4$ alkylthiophenyl" represents a straight or branched chain alkyl group having from one to four carbon atoms attached to a thiophenyl moiety. Typical $C_1-C_4$ alkylthiophenyl groups include methylthiophenyl, ethylthiophenyl, isobutylthiophenyl and the like.

In similar fashion, the term "$C_1-C_4$ alkyloxyphenyl" represents a straight or branched chain alkyl group having from one to four carbon atoms attached to a phenoxy moiety. Typical $C_1-C_4$ alkyloxyphenyl groups include methyloxyphenyl, ethyloxyphenyl, propyloxyphenyl and the like.

PREFERRED COMPOUNDS MADE BY PROCESS OF THE INVENTION

A preferred group of compounds of formula I which can be prepared by the process of the instant invention are those having a substituent pattern independently selected from among the following: Ar is phenyl-substituted with from one to three substituents independently selected from $C_1-C_8$ alkyl, $C_1-C_8$ alkoxy, $C_1-C_4$ alkylphenyl, phenyl, F, Cl, hydroxy, phenoxy, $C_1-C_4$ alkylthiophenyl; and $R^1$, $R^2$ and $R^3$ are each independently hydrogen.

Of this preferred group of compounds, somewhat more preferred compounds of formula I which can be prepared according to the process of the present invention are those compounds wherein Ar is phenyl-substituted with from one to three substituents independently selected from $C_1-C_4$ alkyl, $C_1-C_6$ alkoxy or hydroxy.

Even more preferred compounds of formula I which can be prepared according to the instantly claimed process are those wherein Ar is phenyl-substituted with hydroxy at the 4-position and a $C_1-C_4$ alkyl group at the 3- and 5- positions.

The most preferred compound which can be prepared by the instant process is 5-[3,5-bis(1,1-dimethylethyl)-4-hydroxyphenyl]methyl-4-thiazolidinone.

PROCESS OF THE INVENTION

The process of the present invention provides an improved method for synthesizing the compounds of formula I using inexpensive, readily available reagents and eliminating the generation of excess zinc waste, comprising reacting a 2-thioxo-4-thiazolidinone, a 2,4-thiazolidinedione or a 2-imino-4-thiazolidinone of formula III with an aldehyde of the formula

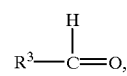

where $R^3$ is as defined above, in the presence of an amine of the formula $H_2NR^6$ where $R^6$ is as previously defined. The process of the invention is illustrated by Scheme I as follows:

Scheme I

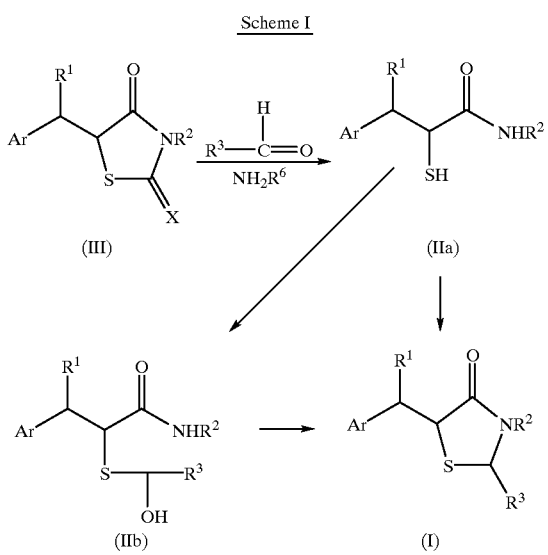

In one pathway of Scheme I, illustrated above, a compound of formula III is dissolved in a liquid medium then mixed with an aldehyde in the presence of an amine to form a compound of formula IIa. IIa reacts further with the aldehyde to form a compound of formula IIb which then cyclizes to form the desired compound of formula I. In an alternate pathway, the compound of formula IIa may react with the aldehyde and amine directly to form compounds of formula I without producing intermediate compound, IIb.

According to the process of the present invention, a 2-thioxo-4-thiazolidinone, 2,4-thiazolidinedione or 2-imino-4-thiazolidnone compound of formula III (starting material) is dissolved in a protic solvent, preferably a low molecular weight alcohol, i.e. an alcohol of the formula HO($C_1$–$C_6$ alkyl). Methanol is preferred in the instantly claimed process. The amount of solvent used should be sufficient to ensure that all compounds stay in solution until the desired reaction is complete.

After the starting material has been dissolved, a low molecular weight amine, (i.e., an amine of the formula $NH_2R^6$ where $R^6$ is hydrogen, $C_1$–$C_6$ alkyl, benzyl or α-methylbenzyl) is added to the reaction mixture to form the thiolamide compound IIa. Ammonia is a preferred amine in the instant process and may be added to the reaction mixture as a gas. The amount of amine is not critical, however, reaction is best accomplished by allowing the 2-thioxo-4-thiazolidinone, 2,4-thiazolidinedione or 2-imino-4-thiazolidinone to react in the presence of a molar excess of the amine relative to the starting material. Preferably 10 to 14 moles of amine are utilized per mole of starting material, formula III.

Upon reaction with an appropriately substituted aldehyde, the thiolamide intermediate, IIa, may first be converted to IIb, which cyclizes to form the desired compound of formula I. In an alternate pathway, the compound of formula IIa may react with the aldehyde and amine directly to form compounds of formula I without producing intermediate compound, IIb. Formaldehyde is preferably employed in quantities of from about 0.5 to about 2.0 moles per mole of starting material, formula III, preferably about 1.1 moles.

Suitable reactants include compounds which convert under the reaction conditions to give aldehyde and amine starting materials, for example, paraformaldehyde, $NH_4OH$, etc.

The process of the present invention is then conducted until substantially all of the 2-thioxo-thiazolidinone, 2,4-thiazolidinedione or 2-imino-4-thiazolidinone starting material has been reacted, and compounds of formula II (vis. IIa and IIb) have been converted to compound I, after about 10 to about 20 hours. Standard analytical techniques, such as HPLC, can be used to monitor the reaction in order to determine when the starting material and intermediates IIa, IIb are converted to product, I.

The desired compound of formula I can be purified using standard crystallization procedures. Preferably, acetic acid is added to the reaction mixture, followed by water as an antisolvent, to effect crystallization of the desired product and increase solubility in methanol of undesired by-products. The solid is then filtered and washed, preferably with water. The recovered product can be reslurried by conventional means. Preferably, the product is reslurried in toluene, ethyl acetate or ethyl acetate/heptane and rinsed with ethyl acetate/heptane to improve purity. Alternately, hexane, or a similar alkane solvent may be substituted for heptane.

Alternately, the recovered product can be dissolved in one of the above listed solvents or solvent mixtures and recrystallized. Crystallization can be enhanced by seeding the solution with a small amount of the desired product.

The process of the present invention can be conducted at any temperature from about 60° C. to about 80° C. If a pressure reactor is employed, superatmospheric pressure and reaction temperature above the boiling point of the reaction medium solvent may be used. The reaction is preferably carried out in a pressure reactor at a temperature of approximately 80° C. for about 17 hour.

In a particularly preferred "one pot" process, the aldehyde and the amine reactants are added in any order or simultaneously with the formula III reactant into a reaction zone, such as a heated reaction vessel having inlet and outlet means, and the reaction is allowed to proceed without isolating compounds of formula IIa or IIb. Reaction is attained by combining (e.g., mixing) the process reactants using conventional agitation means. The process may be run as a batch or continuous process.

Reaction of a thiazolidinone starting material by the process of the present invention generates thiourea as a by-product which is removed during recrystallization. The process of the present invention may also be practiced using either a 2,4-thiazolidinedione or a 2-imino-4-thiazolidinone as the starting material, which eliminates the generation of thiourea as a by-product.

One skilled in the art will recognize that other tautomers of compounds of formula III may be present, particularly when the $R^2$ substituent on compounds of formula III is hydrogen. Therefore, the use of these tautomers as starting materials is contemplated as part of this invention.

The 2-thioxo-4-thiazolidinone, 2,4-thiazoldinedione and 2-imino-4-thiazolidinone starting materials of formula III are either known in the art or can be readily prepared from commercially available aldehydes and rhodanine or thiazolidinediones. For example, Panetta et al., J. Org. Chem. (1992), 57, 4047 prepared 2-thioxo-4-thiazolidinone compounds by condensing rhodanine, or an appropriately substituted rhodanine derivative, with an appropriately substituted aromatic aldehyde or aldehyde derivative in glacial acetic acid using fused sodium acetate as a catalyst then reacting the resultant compound with diethyl 1,4-dihydro-2,6-dimethyl-3,5-pyridinedicarboxylate to produce the thiazolidinone.

The 2,4-thiazolidinedione starting material may be prepared in a similar manner by condensing an appropriately substituted dione derivative with an appropriately substituted aromatic aldehyde or aldehyde derivative in glacial acetic acid using fused sodium acetate as a catalyst then reducing the benzylic double bond with a suitable reducing agent such as hydrogen and palladium on carbon.

The 2-imino-4-thiazolidinone starting material may be prepared by treating a 2-thioxo-4-thiazolidinone compound of formula III with an excess of an amine such as ammonia, then isolating the imine from the reaction mixture by preparative HPLC using silica gel as the stationary phase and ethyl acetate/hexane as the mobile phase.

All other reactants used to prepare the compounds of formulae II and III are commercially available, as are all reagents employed in the process of the present invention.

PREFERRED INTERMEDIATES

Compounds of formula II (IIa and IIb) wherein Ar is phenyl-substituted with from one to three substituents independently selected from $C_1$–$C_8$ alkyl, $C_1$–$C_8$ alkoxy, $C_1$–$C_4$ alkylphenyl, phenyl, F, Cl, hydroxy, phenoxy, $C_1$–$C_4$ alkylthiophenyl, $R^1$ and $R^2$ are hydrogen and $R^5$ is H or —$CHR^3OH$ where $R^3$ is H, are preferred intermediates in the process for preparing compounds of formula I.

Of this preferred group of compounds of formula II, somewhat more preferred are those compounds wherein Ar is phenyl-substituted with from one to three substituents independently selected from $C_1$–$C_4$ alkyl, $C_1$–$C_6$ alkoxy or hydroxy, and $R^5$ is H or —$CHR^3OH$.

Even more preferred are those compounds of formula II wherein Ar is phenyl-substituted with hydroxy at the 4-position and a $C_1$–$C_4$ alkyl group at the 3- and 5-positions, and $R^5$ is H or —$CHR^3OH$ where $R^3$ is as previously defined.

The most preferred compounds of formula II which can be prepared by the instant process are 4-hydroxy-3,5-bis(1,1-dimethylethyl)-α-[(hydroxymethyl)thio]benzene ethanamide and 4-hydroxy-α-mercapto-3,5-(1,1-dimethylethyl) benzene ethanamide.

METHOD OF MAKING THE INTERMEDIATES

The compounds of formula II are prepared according to the following general procedure:

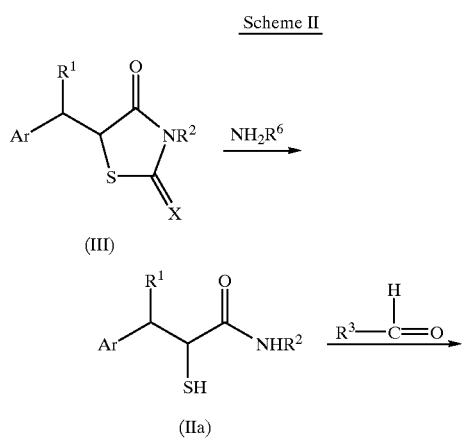

Scheme II

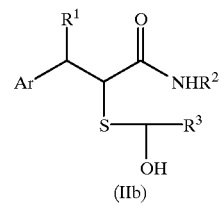

(IIb)

In the above Scheme II, a thiocarbonyl, dione or imine derivative of formula III is treated with an amine of the formula $NH_2R^6$, where $R^6$ is as previously defined, in a protic solvent such as water or a $C_1$–$C_6$ alcohol to provide a thiolamide of formula IIa. Water is the preferred reaction medium in the instant process.

The reaction can be conducted at any temperature between about 60° C. and 100° C., for a period of about 12 to 36 hours, preferably at 90° C. for 12 hours.

Ammonia is a preferred amine in the instant process. The amount of amine is not critical, however, reaction is best accomplished by allowing the 2-thioxo-4-thiazolidinone, 2,4-thiazolidinedione or 2-imino-thiazolidinone to react in the presence of a molar excess of the amine relative to the starting material. Preferably 10 to 14 moles of amine per mole of formula III starting material are utilized.

The desired thiolamide compound of formula IIa can be purified using standard recrystallization procedures in a suitable organic solvent, preferably toluene or ethyl acetate/heptane mixtures.

The thiolamide, IIa, can be readily converted to the hemithioacetal, IIb by mixing in a suitable quantity of polar solvent such as water, acetone or dioxane to form a slurry, (preferably acetone) then reacting with an aldehyde of the formula

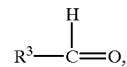

where $R^3$ is as defined above. Formaldehyde is preferably employed as the aldehyde in quantities of from about 0.9 to about 1.2 moles relative to the starting material, preferable about 1.1 moles. One to three moles (relative to the thiolamide) of a suitable inorganic mineral acid such as hydrochloric acid or organic acid, such as paratoluenesulfonic acid is added as a catalyst. The reaction is preferably conducted at temperatures from about 20° C. to about 30° C. for about 15 minutes to 12 hours, preferably at 25° C. for 1 hour. The reaction product can then be filtered and washed with water.

The compounds of formula II are useful as intermediates for preparing compounds of formula I.

The following examples further illustrate the process of the present invention. The examples also illustrate the preparation of the compounds of this invention as well as the compounds used in the method of this invention. The examples are illustrative only and are not intended to limit the scope of the invention in any way.

EXAMPLE 1

This Example illustrates the process of the invention.
Preparation of 5-[3,5-bis(1,1-dimethylethyl)-4-hydroxyphenyl]methyl-4-thiazolidinone To 3.22 g (9.2 mmol) of 5-{[3,5-bis(1,1-dimethylethyl)-4-hydroxyphenyl]}-methyl-2-thioxo-4-thiazolidinone, in a 25 mL pressure tube equipped with magnetic stir bar, 13 mL of methanol was added. The resulting reaction mixture was cooled to 0° C. and ammonia gas (1.6 g, 91 mmol) was slowly added. Formalin (0.76 mL, 0.8 g, 10 mmol) was then added. The pressure tube was sealed and heated to 80° C. for approximately 17 hours with stirring. Reaction was deemed complete when the amount of thiolamide was below 4%, as determined by HPLC. Deionized water (12 mL) was then added in a drop-wise manner, followed by acetic acid (6 mL). After 30 min, the reaction mixture was cooled to 0° C. for 1 hour. The reaction mixture was filtered and the resulting crystalline product was dissolved in ethyl acetate (5 vol). Dissolution was facilitated by heating to 66° C. The resulting solution was filtered and seeded with a small amount of 5-[3,5-bis(1,1-dimethylethyl)-4-hydroxyphenyl] methyl-4-thiazolidinone as the solution was slowly cooled to ambient temperature. Crystallization ensued and the resultant slurry was stirred for approximately 4 hours. The slurry was concentrated under reduced pressure (1 vol ethyl acetate) and stirred for an additional 16 hours. The slurry was filtered and the wet cake was washed with water (2×10 mL) and ¼ ethyl acetate/hexane (2×10 mL). The product was dried in an oven at 50° C. to obtain 2.07 g (70% yield) of title compound.

EXAMPLE 2

This Example describes the process of the invention and the preparation of compounds of formula III.
Preparation of 5-[3,5-bis(1,1-dimethylethyl)-4-hydroxyphenyl]methyl-4-thiazolidinone
A.
5-{[3,5-bis(1,1-dimethylethyl)-4-hydroxyphenyl]}methylene-2,4-thiazolidinedione To a flask containing 41.7 g (0.18 moles) of 3,5-di-tert-butyl-4-hydroxybenzaldehyde, 25 g (0.21 moles) of 2,4-thiazolidinedione and 29.5 g (0.36 moles) of anhydrous sodium acetate were added. To these solids 175 ml of glacial acetic acid was added and the mixture was stirred and refluxed for 18 hours. The mixture was allowed to cool to room temperature and the precipitated solid was collected by filtration. The precipitate was rinsed with 1:1 water/ethanol then dried. The dried solid was slurried in 300 ml of methylene chloride for five hours, then collected and dried to yield 38.7 g of the sub-titled intermediate.

B. 5-[3,5-bis(1,1-dimethylethyl)-4-hydroxyphenyl]methyl-2,4-thiazolidinedione

To 15.0 g (0.045 moles) of 5-{[3,5-bis(1,1-dimethylethyl)-4-hydroxyphenyl]} methylene-2,4-thiazolidinedione, in 375 ml of ethyl acetate, 3.0 g of 10% palladium on carbon was added. The mixture was heated at 80° C. in the presence of 50 psi (345 KPa) of hydrogen for 4.5 hours. An additional 3.0 g of 10% palladium on carbon was added and the mixture was again heated at 80° C. in the presence of 50 psi (345 KPa) of hydrogen for 2 hours. The catalyst was removed by filtration and the filtrate was evaporated to afford a solid. The solid was recrystallized from toluene and dried at 60° C. to obtain 8.93 g (59% yield) of subtitled compound.

C. 5-[3,5-bis-(1,1-dimethylethyl)-4-hydroxyphenyl}methyl-4-thiazolidinone

To 2.78 g (9.2 mmol) of 5-{[3,5-bis(1,1-dimethylethyl]-4-hydroxyphenyl]}-methyl-2,4-thiazolidinedione in a pressure tube, 13 ml of methanol was added. The mixture was cooled to 0–5° C. and 2.2 g (130 mmol) of ammonia and 0.76 ml (10 mmol) of formalin (aqueous formaldehyde) was added. The tube was sealed and heated to 80° C., while stirring, for 20 hours. The mixture was cooled to ambient temperature, then subjected to flash column chromatography using 1:1 ethyl acetate:heptane. Analysis by $^1$H-NMR and HPLC indicated 60% of the sample was the title compound.

EXAMPLE 3

This Example describes the process of the invention and the preparation of compounds of formula III.
Preparation of 5-[3,5-bis(1,1-dimethylethyl)-4-hydroxyphenyl]methyl-4-thiazolidinone
A. 5{[4-hydroxy-3,5-bis(1,1-dimethylethyl)phenyl]methyl}2-imino-4-thiazolidione A mixture of 50 gm of 5-{[3,5-bis(1,1-dimethylethyl)-4-hydroxyphenyl]}-methyl-2-thioxo-4-thiazolidinone and 285 mL of concentrated ammonium hydroxide was slowly warmed to reflux in a flask fitted with a condenser/dry ice condenser. After two hours of warming, the dry ice was allowed to melt and the temperature was raised to 97° C. This temperature was maintained for 15 hours. The reaction mixture was cooled to 10° C. and the resulting white crystals were collected by filtration. The filter cake was washed with deionized water and dried under vacuum at 60° C. The subtitled compound was isolated from the white crystals by preparative HPLC using silica gel as the stationary phase and ethyl acetate/hexane as the mobile phase.

Mass spec, M$^+$=334; Elemental analysis: Theory: C,64.64 H, 7.84 N, 8.38 Found C, 65.67 H, 7.76 N, 8.64.

B. 5-[3,5-bis(1,1-dimethylethyl)-4-hydroxyphenyl]methyl-4-thiazolidinone

To 0.265 g of 5{[4-hydroxy-3,5-bis(1,1-dimethylethyl)phenyl]methyl}2-imino-4-thiazolidione in 1.3 mL of methanol was added 1.0 mL of methanol, which had been saturated with ammonia gas, and 0.08 mL of aqueous formaldehyde (formalin). The mixture was sealed and heated at 80° C. overnight. Formation of 5-[3,5-bis(1,1-dimethylethyl)-4-hydroxyphenyl]methyl-4-thiazolidinone was confirmed by HPLC retention time comparison with a standard and coinjection. HPLC versus a potency reference standard indicated that the yield was approximately 39%.

EXAMPLE 4

This Example describes the preparation of 4-hydroxy-α-mercapto-3,5-(1,1-dimethylethyl)benzene-ethanamide (thiolamide IIa).

A mixture of 50 gm of 5-{[3,5-bis(1,1-dimethylethyl)-4-hydroxyphenyl]}-methyl-2-thioxo-4-thiazolidinone and 285 mL of concentrated ammonium hydroxide was slowly warmed to reflux in a flask fitted with a condenser/dry ice condenser. After two hours of warming, the dry ice was allowed to melt and the temperature was raised to 97° C. This temperature was maintained for 15 hours. The reaction mixture was cooled to 10° C. and the resulting white crystals were collected by filtration. The filter cake was washed with deionized water and dried under vacuum at 60° C. to obtain 40.3 g of title product (91.5% yield).

Mass spec, M$^+$=309; Elemental analysis: Theory: C, 65.98 H, 8.79 N, 4.53; Found: C, 65.50 H, 8.83 N, 4.65

EXAMPLE 5

This Example describes the preparation of 5-[3,5-bis-(1,1-dimethylethyl)-4-hydroxyphenyl}methyl-4-thiazolidinone from thiolamide IIa.

To a 25 mL pressure tube equipped with magnetic stir bar, 2.85 g (9.2 mmol) of 4-hydroxy-α-mercapto-3,5-(1,1-dimethylethyl)benzene-ethanamide and 13 ml of methanol was added. The resulting reaction mixture was cooled to 0° C. and ammonia (1.6 g, 91 mmol) was slowly added.

Formalin (0.76 mL, 0.8 g, 10 mmol) was then added and the pressure tube was sealed and heated to 80° C. for approximately 8 hours. Deionized water (12 mL) was then added in a dropwise manner followed by acetic acid (6 mL). After 30 min, the reaction mixture was cooled to 0° C. for 1 hour. The resulting crystalline slurry was filtered, washed with H₂O (10 mL) and dried at 40° C. to afford 1.69 g of title product in 57% yield.

EXAMPLE 6

This Example describes the preparation of 4-hydroxy-3,5-bis(1,1-dimethylethyl)-α-[(hydroxymethyl)-thio]benzene ethanamide. (hemithioacetal, IIb)

Hydrochloric acid (conc) (0.6 mL, 7.24 mmol, 2.0 eq) was added to a slurry of 4-hydroxy-α-mercapto-3,5-(1,1-dimethylethyl)benzene-ethanamide (1.12 gm, 3.62 mmol) in 5 mL of deionized water and 0.54 mL (7.24 mmol, 2.0 eq) of formalin. The slurry thinned out and then became thick again. After stirring overnight at room temperature, the resulting slurry was filtered and the filter cake was washed with deionized water to give 1.2 g of title product (97% yield) as a white crystal.

Mass spec, M⁺=339; Elemental Analysis: Theory: C, 63.68 H; 8.61 N, 4.13 S, 9.44; Found: C, 63.98 H, 8.52 N, 4.26 S, 9.54.

EXAMPLE 7

This Example describes the preparation of 5-[3,5-bis(1,1-dimethylethyl)-4-hydroxyphenyl]methyl-4-thiazolidinone from hemithioacetal, IIb.

4-hydroxy-3,5-bis(1,1-dimethylethyl)-α-[(hydroxymethyl)-thio]benzene ethanamide. (3.0 gm) in 10 mL of methanol was cooled to 0° C. and the resulting solution was saturated with anhydrous ammonia gas. The reaction mixture was then placed in a sealed tube and warmed in an oil bath to 60° C. After stirring in the sealed tube overnight at 60° C., the reaction mixture was cooled to room temperature and the resulting slurry was filtered and washed with methanol. The resulting filter cake was dried under vacuum to give 2.5 gm of title compound (88% yield).

We claim:

1. A compound of the formula II

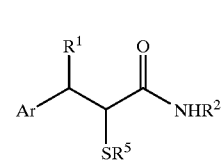

(II)

wherein:

Ar is (i) phenyl, (ii) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, Cl, hydroxy, phenoxy, $C_1$–$C_4$ alkyloxyphenyl, thiophenyl, $C_1$–$C_4$ alkylthiophenyl, $N(R^4)_2$ where each $R^4$ is independently $C_1$–$C_6$ alkyl or (iii) 1- or 2-napthyl;

$R^1$ is hydrogen $C_1$–$C_6$ alkyl, $C_1$–$C_4$ alkylphenyl, phenyl or phenyl-substituted with one or two substituents independently selected from Cl, F, $C_1$–$C_4$ alkyl, $C_1$–$C_4$ alkoxy, trifluoromethyl, —N($C_1$–$C_4$ alkyl)₂ or $C_1$–$C_4$ alkylthio;

$R^2$ is H, $C_1$–$C_6$ alkyl, benzyl or α-methylbenzyl; and $R^5$ is H or —CHR³OH, where $R^3$ is (i) H, (ii) $C_1$–$C_6$ alkyl, (iii) phenyl, (iv) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, Cl, hydroxy, phenoxy, $C_1$–$C_4$ alkyloxyphenyl, thiophenyl, $C_1$–$C_4$ alkylthiophenyl, $N(R^4)_2$ where each $R^4$ is independently $C_1$–$C_6$ alkyl or (v) 1- or 2-napthyl.

2. The compound of claim 1 wherein Ar is phenyl-substituted with from one to three substituents independently selected from $C_1$–$C_8$ alkyl, $C_1$–$C_8$ alkoxy, $C_1$–$C_4$ alkylphenyl, phenyl, F, Cl, hydroxy, phenoxy or $C_1$–$C_4$ alkylthiophenyl;

$R^2$ is H; and $R^5$ is H or —CH₂OH.

3. The compound of claim 2 which is 4-hydroxy-3,5-bis(1,1-dimethylethyl)-α-[(hydroxymethyl)-thio]benzene ethanamide.

4. The compound of claim 2 which is 4-hydroxy-α-mercapto-3,5-(1,1-dimethylethyl)benzene ethanamide.

* * * * *